United States Patent
Dunias et al.

(10) Patent No.: US 9,681,826 B2
(45) Date of Patent: Jun. 20, 2017

(54) METHOD, DEVICE AND SYSTEM FOR MEASURING TORSION OR BENDING AT A JOINT BETWEEN TWO LIMBS

(75) Inventors: Paraskevas Dunias, Eindhoven (NL); Andrew Statham, Eindhoven (NL); Gerardus Johannes Nicolaas Doodeman, Veldhoven (NL); Anmin Jin, Eindhoven (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 973 days.

(21) Appl. No.: 13/576,670

(22) PCT Filed: Feb. 3, 2011

(86) PCT No.: PCT/NL2011/050074
§ 371 (c)(1),
(2), (4) Date: Sep. 7, 2012

(87) PCT Pub. No.: WO2011/096804
PCT Pub. Date: Aug. 11, 2011

(65) Prior Publication Data
US 2013/0131554 A1     May 23, 2013

(30) Foreign Application Priority Data
Feb. 3, 2010   (EP) ..................................... 10152569

(51) Int. Cl.
*A61B 5/103* (2006.01)
*A61B 5/117* (2016.01)
(Continued)

(52) U.S. Cl.
CPC .............. *A61B 5/11* (2013.01); *A61B 5/1071* (2013.01); *A61B 5/45* (2013.01); *A61B 5/1121* (2013.01);
(Continued)

(58) Field of Classification Search
CPC ..... A61B 5/4528; A61B 5/1071; A61B 5/103; A61B 2562/0261; A61B 5/1121;
(Continued)

(56) References Cited

U.S. PATENT DOCUMENTS

| 4,648,407 A | 3/1987 | Sackner |
| 4,940,063 A | 7/1990 | Challis |

(Continued)

FOREIGN PATENT DOCUMENTS

| CN | 2422938 Y | 3/2001 |
| DE | 3532520 A1 | 3/1987 |

(Continued)

OTHER PUBLICATIONS

International Search Report, PCT/NL2011/050074, Mailing date: Jun. 8, 2011.
(Continued)

*Primary Examiner* — Devin Henson
(74) *Attorney, Agent, or Firm* — Banner & Witcoff, Ltd.

(57) ABSTRACT

Method, device and system for measuring a degree of torsion or bending of a joint. The method comprises the steps of attaching a sensor (56) to the limbs that are joined by the joint, measuring an output signal of the sensor during torsion or bending at the joint, and a final step of relating said output signal of the sensor to a degree of torsion or bending. The sensor comprises an electrically conductive loop (51), with loop parts that run from one limb to other and back in the loop, the area of said loop at least partially covering both limbs from one limb to the other. The limbs may be limbs of the human or animal body, for instance limbs at a knee. The sensor further comprises an output unit (57) for providing an output signal that is a measure for the inductance of the loop. Calibration data for the sensor may be determined by detecting the output signal of the sensor for a well defined degree of torsion or bending at said joint under static conditions and storing the calibration data.

18 Claims, 9 Drawing Sheets

(51) Int. Cl.
*A61B 5/11* (2006.01)
*A61B 5/107* (2006.01)
*A61B 5/00* (2006.01)

(52) U.S. Cl.
CPC .......... *A61B 5/1122* (2013.01); *A61B 5/4528* (2013.01); *A61B 5/6828* (2013.01); *A61B 2503/10* (2013.01); *A61B 2505/09* (2013.01)

(58) Field of Classification Search
CPC ..... A61B 5/1122; A61B 5/6828; A01D 5/165; A01D 5/1655; A01D 5/20; A01D 5/2006; A01D 5/202; A01D 5/2026
USPC ........................................................ 600/595
See application file for complete search history.

(56) References Cited

U.S. PATENT DOCUMENTS

| | | | | |
|---|---|---|---|---|
| 5,867,022 | A * | 2/1999 | Eden et al. | 324/207.16 |
| 6,360,615 | B1 * | 3/2002 | Smela | A61B 5/1124 73/862.474 |
| 2009/0018428 | A1 | 1/2009 | Dias et al. | |
| 2009/0024065 | A1 | 1/2009 | Einarsson | |
| 2009/0025483 | A1 * | 1/2009 | Connor et al. | 73/849 |
| 2009/0095094 | A1 * | 4/2009 | Helmer et al. | 73/865.4 |

FOREIGN PATENT DOCUMENTS

| | | |
|---|---|---|
| EP | 2 057 944 A1 | 5/2009 |
| JP | 2006017680 A | 1/2006 |
| JP | 2007075234 A | 3/2007 |

OTHER PUBLICATIONS

Kwang Yong Lim; Goh Fyk; Wei Dong; Kim Doang Nguyen; I-Ming Chen; Song Huat Yeo; Duh HBL; Chung Gon Kim: "A wearable, self-calibrating, wireless sensor network for body motion processing" XP002580464, 2008 IEEE International Conference on Robotics and Automation, Pasadena, CA, USA, May 19-23, 2008.

Wijesiriwardana R: "Inductive fiber-meshed strain and displacement transducers for respiratory measuring systems and motion capturing systems" XP002580465, IEEE Sensors Journal, vol. 6, No. 3, Jun. 2006.

* cited by examiner

METHOD, DEVICE AND SYSTEM FOR MEASURING TORSION OR BENDING AT A JOINT BETWEEN TWO LIMBS

CROSS-REFERENCE TO RELATED APPLICATIONS

This application is a U.S. National Stage application under 35 U.S.C. §371 of International Application PCT/NL2011/050074 (published as WO 2011/096804 A1), filed Feb. 3, 2011 which claims priority to Application EP 10152569.9, filed Feb. 3, 2010. Benefit of the filing date of each of these prior applications is hereby claimed. Each of these prior applications is hereby incorporated by reference in its entirety.

FIELD OF THE INVENTION

The invention relates to a method for measuring a degree of torsion or bending at a joint between two limbs, for example of a part of a human or animal body. The invention also relates to a system for measuring a degree of torsion or bending. Further the invention relates to a brace for measuring a degree of torsion or bending.

BACKGROUND

Measuring torsion or bending of a part of the human or animal body, for example a knee or a neck may be of importance for science or therapy. Information obtained by such a measurement can be used to improve human or animal performance, for example in sports, and it may be used to prevent injuries caused by straining.

A body motion sensor is described in an article by Ravindra Wijesiriwardana, titled "Inductice Fiber-Meshed Strain and Displacement Transducers for Respiratory Measuring Systems and Motion Capturing Systems", published in the IEEE sensors journal Vol 6, No 3 (kune 2006) pages 571-579. (EPO reference XP-002580465). This article proposes the use of electroconductive coils integrated into garments as transducers for measuring human limb motion. The coils are made by knitting conductive fibres into the fabric of garments. A coil with windings around the arm is described, with windings below the elbow, windings at the elbow and windings above the elbow. Measurement of the self inductance of a single coil comprising all windings or mutual inductance between coils with parts of the windings were used to measure bending of the elbow.

This makes it possible to measure the angle of the bend between two points above and below the elbow joint, when joint angle is approximated from measuring above and below the joint, the fulcrum or axis of rotation is assumed to be consistent between subjects, by monitoring the bend over the whole joint, differences or changes in the fulcrum or axis of rotation are included in the measurement. However, with this coil configuration it is difficult to measure whole bending. The mutual inductance sensor cannot measure the degree of rotation which can be a very important element in biomechanics of joints for example. The article is silent about the use of additional sensors.

EP 2 057 944 discloses a knee brace with a combination of an acceleration sensor and a optical fibre that is used as a device (goniometer) for measuring bending angle.

International patent application WO 2009/061181 discloses a method, a brace and a system for measuring an angle between a first and a second member, which elements may be pivoting limbs of humans or animals, like knee joints. With this known method an angle measuring sensor suitable for use under dynamic situations, is calibrated in a static situation by means of accelerometers. Said patent application discloses the use of an optical goniometer as an angle measuring sensor. More in particular it discloses the use of optical fibres or optical flexible tubes for measuring an angle.

A problem in using optical fibres for measuring an angle is that the degree of bending is limited to maximum angles of about 30 degrees due to possible cracking at larger angles and due to the fact that the light transmittance is only possible at relatively small angles. Further are such optical fibres fragile and prone to mechanical damage for instance of the so-called cladding layer, resulting in less accuracy and reduced performance, in particular reliability.

A network of body sensors is disclosed in an article by Kwang Yong Lim et al. titled "A Wearable, Self Calibrating. Wireless Sensor Network for Body Motion Processing", published in the proceedings of the 2008 IEEE International Conference on Robotics and Automation, Pasadena, Calif., USA, May 19-23, 2008, pages 1017-1022 (EPO reference XP00258040464). Transmitters are used to transmit data from a plurality of motion sensors by wireless signal to a central processor. The article mentions a range of possible sensors, including accelerometers, a 3-axis magnetic sensor, gyroscopes and a linear encoder. More generally the article mentions that mechanical, inertial, acoustic, magnetic and optical sensing can be used, as well as fibre mesh sensing optical fibre loss, piezo-electric fabrics. The article describes a method of mathematical modelling of the output information from such sensors and fusion of the information from different sensors. Only the construction of the linear encoder is described in some detail.

SUMMARY

It is an objective of the present invention to provide a sensor and sensing method that is sensitive to torsion and bending of a joint.

A method according to claim 1 is provided. A sensor is used that comprises an electrically conductive loop, the area of said loop extending from one limb at a joint to the other. An output unit is used to providing an output signal derived from the loop.

By using a loop with a loop area that extends to both limbs, rather than only a plurality of loops detection of a wide range of bending and torsioning motion of the limbs relative to each other is made possible. Compared to the solution with only a plurality of loops that each run around a single limb, with loop areas perpendicular to the axial direction of the limbs, more different kinds of joint motion can be detected. The conductive loop may be part of an inductance with one or a plurality of conductive loops. As used herein, the loop area corresponds to the area within one winding of such an inductance. However, the loop areas of a plurality of windings may coincide substantially, the plurality of loop areas extending from one limb at the joint to the other.

In an embodiment the electrically conductive loop runs entirely on one side of the joint and limbs, i.e. so that the limbs do not run through the loop area at all. This makes is possible to detect a wide range of joint motion. In another embodiment, parts of the loop on respectives limbs runs on surface of those limbs that face in mutually opposite directions. Thus, apart from extending from one limb to the other, the loop also runs in such a way that the limbs run through the loop area. This increases sensitivity of the sensor.

In an embodiment a self inductance is measured of the electrically conductive loop formed by the first, second, third and fourth loop parts, or a plurality of such loops. Alternatively, the inductance matrix of a plurality of loop or loop parts could be measures, i.e. the cross inductance (voltage induced in one loop by current in other loop or loop part) as well as the self inductance of these loops or loop parts. From the inductance matrix the self inductance of combinations of the loop or loop parts may be determined. Use of the self inductance to measure joint motion simplifies the measurement.

In an embodiment the device is provided with an additional sensor for calibrating the relation between the output from the conductor loop and joint angles etc.

An advantage of an electrically conductive loop is that such a loop can be made mechanically very flexible and that bending with large angles is possible without damaging the loop. An effect of using a flexible loop is that the sensor can be deformed to a large extent without being damaged.

The large deformation of the sensor allows measuring a large bending or torsion of a knee, an elbow or other parts of the human or animal body for example the torso or neck.

BRIEF DESCRIPTION OF THE FIGURES

These and other objects and advantageous aspects will become apparent from a description of exemplary embodiments, using the following figures

DETAILED DESCRIPTION EXEMPLARY EMBODIMENTS

Figure 1:
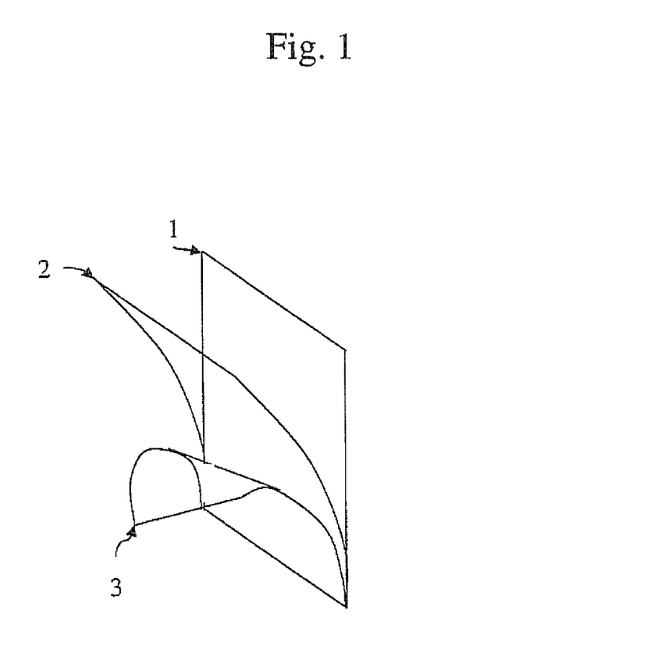
FIG. 1 shows schematically two different deformations of a loop.

Bending is a characteristic of joints like a knee or an elbow. Torsion is characteristic for rotating elements of the body like for example the torso or the neck. In particular neck and torso motions can be complex because they have more than one degree of freedom. A sensor is provided that allows the measurement of such complex motions. In FIG. 1 a simple bending (2) and a more complex deformation (3) of a rectangle (1) are shown. Each of the shapes of the rectangular shaped loop will have a different inductance. Consequently, the inductance of the loop is a measure for the deformation.

The method for measuring a degree of torsion or bending comprises three steps, wherein the second step comprises sub-steps. Two of theses sub-steps can be performed in an arbitrary order. In the first step, a sensor is attached to the part of the body of which the torsion or bending has to be measured. In the final step of the method, a measured output signal of the sensor is related to a degree of torsion or bending of the part of the body under measurement. In particular this will be a torsion or bending in a dynamic situation, viz. when the human or animal is in motion. In between these two steps the sensor is calibrated, preferably at a moment when the human or animal is in rest. Calibration means that the inductance of the loop is related to a specific well defined torsion or bending. These calibration data have to be stored for later use in the final step of relating a measured inductance to a torsion or bending. In this intermediate step of the method, the inductance of the loop is also measured in the dynamic situation. It is not relevant whether the calibration is performed before the dynamic measurement or afterwards. Of course, the storing of the calibration data has to be done after the calibration step itself.

Calibration

The method is based on the insight that some type of sensors for measuring torsion and bending have a better performance in a dynamic situation and that other types of sensors are better suited for use in a static situation. In general, the torsion or bending, that can be translated to bending angles and angles of rotation, can be measured rather well and accurately with well known angle measurements in a static situation. Such measurements can be performed by hand or by automated or semi-automated technical means of all kinds Measuring by hand can be either directly at the body or on the basis of photographs, film, or video. Measuring in a static situation can also be done by using a potentiometer, a variable resistor, an accelerometer or other technical means for measuring an angle either directly or indirectly by determining for example the direction of the gravitational force relative to the position of the bending element. However, most of these methods can not be used in a dynamic situation, for example because the measuring equipment is too large or too heavy to be attached to a moving body.

Sensors for measuring the torsion or bending in a dynamic situation may be less accurate because of, for example, drift or because they are particularly suited for performing relative measurements, not for absolute measurements. In the method, brace and system, a conductive loop is used for measuring the torsion or bending. Because the inductance of the loop is not an absolute measure for its shape, more in particular its way of torsion or bending, such a loop requires calibration.

The calibration can be performed according to several methods. The calibration can precede the actual measurement of the torsion or bending. In such a situation the calibration data can be used to determine the torsion and bending in real time. The calibration can also succeed the actual measurement of the torsion and the bending. In this latter situation, the measured data have to be stored and processed afterwards to obtain the torsion or bending during the actual measurement. However, a preferred method is a recurring calibration during the actual measurement. Such a recurring calibration, which might be implemented to be performed automatically, allows correction for semi-permanent changes in the geometry of the conductive loop. Changes in the geometry of the loop may origin for example from a shift of the brace during use. An automatic recurring calibration may be triggered by an accelerometer detecting that the human or the animal is in a rest position, or at least that the part of the body for which the torsion or bending has to be measured is in rest.

In the situation of recurring calibration during the actual measurement, one or more additional sensors have to be attached to the body. Such additional sensors should be sensors able to determine the torsion or bending accurately in the static situation, viz. in the situation where the body or at least the relevant part of the body is in rest. In practice such sensors may be acceleration sensors, viz. sensors that can detect the direction of the gravitational force, and therefore allow accurate angle measurements. Two additional angle measurement sensors may be attached at the two outer ends of the bending part, for example at the upper and lower leg when bending of a knee has to be measured.

The Loop

Figure 2:
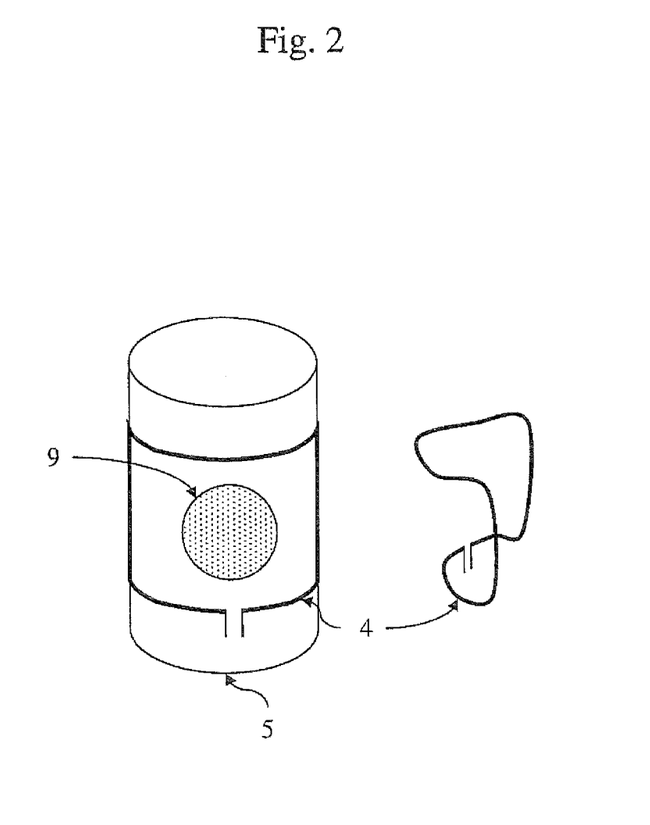
FIG. 2 shows schematically an example of an embodiment of a loop for a knee-brace.

The inductance of an electrically conductive loop varies when the shape of the loop changes, for example by bending, stretching, twisting or other deformation. However, it is sometimes difficult to relate the variation in the inductance to a specific change in the shape of the track. For this reason the loop is preferably constructed in a particular shape or its deformation is restricted by the nature of the body or by clothing or brace. In such a situation the measured inductance will correlate well with the torsion or bending obtained at the calibration step. In FIG. 2 an example of an embodiment of a loop (4) for a knee-brace (5) is shown. The brace is represented here as a cylinder but in practice the shape of the brace will be better adapted to fit to the lower and upper leg and the knee. An indication of the size of the knee is given by a circle (9). At the right hand side of the figure a three-dimensional representation of the loop only, is shown. Here it can be seen that the loop is adapted to a specific shape of under and upper leg and knee, which shape is observed to have an improved sensitivity.

In case there are more degrees of freedom, monitoring characteristics of the change in inductance of the loop, rather than just a single isolated inductance measurement, can help to differentiate which movement is performed so as to be able to isolate forward and lateral bending and rotation. Additional loops can be used to detect more complex deformations, viz. deformations with more than one degree of freedom. More in particular, such additional loops or the area of these loops can be situated perpendicular to the area of the first loop to optimize for measuring more than one degree of freedom.

The conductive loop may be attached to or integrated into various materials, in particular fabrics or plastics to suit different applications e.g. more elastic materials that provide pretension to the sensor. However, the loop can also be attached to the body by for example an adhesive or by clamping to clothes. The loop can be shaped so as to obtain a maximum sensitivity and accuracy for a specific torsion or bending. The loop may have a simple shape like a rectangle or a circle, or it may have a more complex shape that encloses a part of the body as is shown in the right hand site of FIG. 2. In the drawings, the loop is presented as a single open winding. However, to increase sensitivity or for other reasons improving the performance, the loop may consist of two or more windings.

An ideal or perfect loop may be electrically characterised by its inductance. However, a more accurate characterisation of a loop is the frequency dependent complex impedance or admittance. Where in this document the term inductance of the loop is used, it should be understood that this term includes, more generally, the electrical impedance of the loop.

Figure 3:
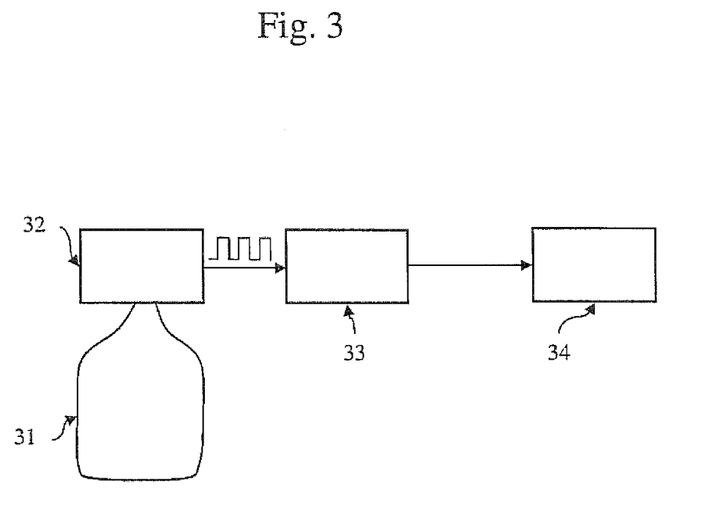
FIG. 3 shows schematically a possible set-up for measuring the inductance of the loop.

As illustrated in FIG. 3, the inductance of a loop (32) can be measured with equipment known to those skilled in the art. It can be measured with a frequency counter (33) by using an oscillator circuit (32) as shown schematically in FIG. 3. The output signal of the counter may be send to a data logger (34).

The Brace

A brace, more in particular an orthopeadic brace, is a product that can be used, among others, for supporting parts of a body. Braces are also used for partly immobilizing parts of a human or animal body, in particular in joints like for example a knee. Braces can also be used for supporting or correcting for example the movement of the human torso. Braces can be made out of several types of materials depending on the specific application and demand. Knee braces, for example, can be made of an elastic material, more in particular a fabric, to allow easy fitting to different persons. However, braces can also be custom made to fit a specific person. Such braces can be made out of a plastic material and may even comprise metallic or ceramic parts. Often the brace will allow one or more degrees of freedom in the motion of the body element. Flexible braces, either made out of a flexible material, or comprising joints can be used for therapeutic reasons and other type of use, for example in sports.

For therapeutic or other reasons, for example for scientific research related to the movement of humans or related to the load on joints or other bending or torsion elements of the body, such a torsion or bending has to be measured under specific conditions. It has been observed that using an electrically conductive loop for measuring the torsion and bending of parts of a human or animal body has advantages over for instance optical methods and systems. In the exemplary method, such a loop may be attached directly to the part of the body by means of for example an adhesive, however using a brace is preferred in particular if the motion has to be supported, corrected, or stimulated.

A brace can not only, and even not in the first place, be used for attaching sensors to the body, but also for limiting the degree of freedom to force a proper use of for example a joint or to relieve forces.

Figure 4:
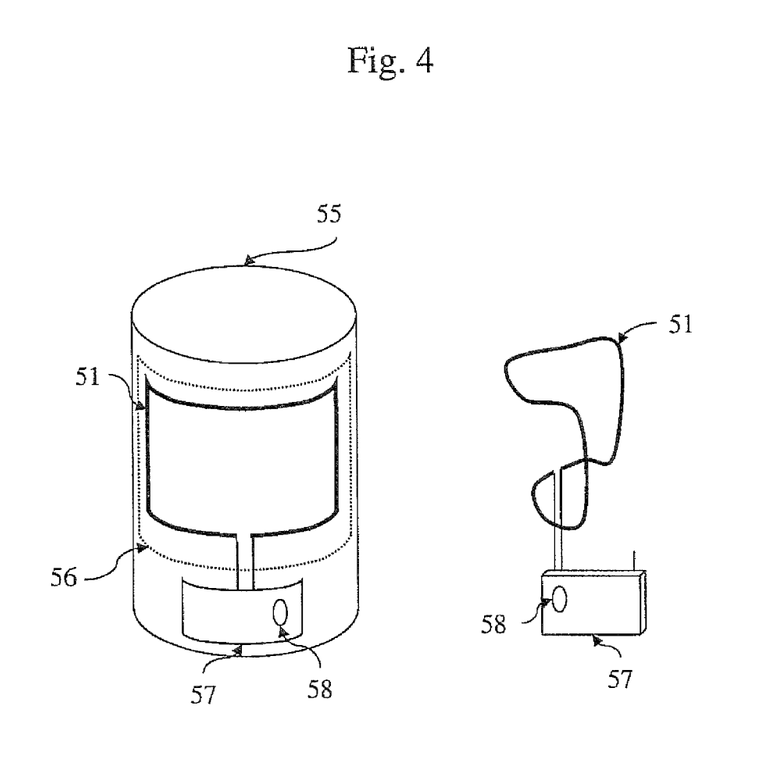
FIG. 4 shows schematically an embodiment of a brace

An embodiment of a brace is shown in FIG. 4. The brace (55) shown schematically as a cylinder comprises a sensor (56) for measuring a degree of torsion or bending and a transmitter (57) for sending an output signal of the sensor. Although the sending may be via wires of fibers, a wireless transmitter (57) is preferred to prevent the measurement or movement being disturbed. The sensor comprises an electrically conductive loop (51) for covering the part of the body for which the torsion or bending has to be measured. The transmitter further comprises an output unit (58) for providing an output signal that is a measure for the inductance of the loop. The output unit may comprise an electronic circuit, or eventually an electro-optical circuit.

Figure 5:
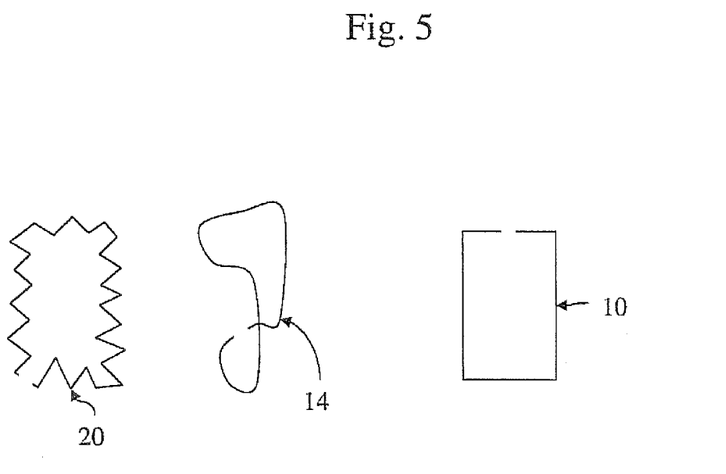
FIG. 5 shows some embodiments of a loop for measuring torsion or bending.

The conductive loop may be attached to a flexible brace or other mounting substrate that allows the track to be attached to the part of the body for which the torsion or bending has to be measured. The conductive loop may preferably be constructed from metallic wire, carbon fiber or any other type of flexible conductive wire or fiber. The wire or fiber may be weaved, knitted or "zig-zagged" to the substrate allowing more flexibility and to allow a good integration with the fabric or other material from which the substrate is fabricated. However, the conductive loop may also be printed or laminated on the substrate material. In FIG. 5 three possible embodiments of the loop are shown. The rectangle (10) may satisfy for simple bending with a small angle. For situations in which the wire or fiber of the loop cannot be stretched, the wire or fiber may have a "zig-zag" shape (20) that allows the loop to follow a stretching of the brace. A shape (14) rather similar to the one that has been shown to have advantageous properties for measuring the bending of a knee might also be used for measuring the torsion of the torso. The dimensions of the loop have of course to be adapted to the difference in size between a knee and a torso.

The brace is suitable for use in the method. However, there might be circumstances where one is only interested in a relative bending or torsion of a part of the human or animal body. In such a situation, a calibration might not be necessary. The relative variations in the inductance of the loop may provide sufficient information for the user. In such a situation the brace can be used for a method for measuring a degree of torsion or bending of a part of a human or animal body, the method comprising a first step of attaching a sensor for measuring the degree of torsion or bending to said part of the human or animal body, a second step comprising measuring an output signal of the sensor during torsion or bending of said part of the human or animal body, and a final step of relating said output signal of the sensor to a degree of torsion or bending by using the calibration data. Such a method may be characterised in that the sensor comprises an electrically conductive loop, the area of said loop at least partially covering said part of the human or animal body, and an output unit for providing an output signal that is a measure for the inductance of the loop.

Figure 6:
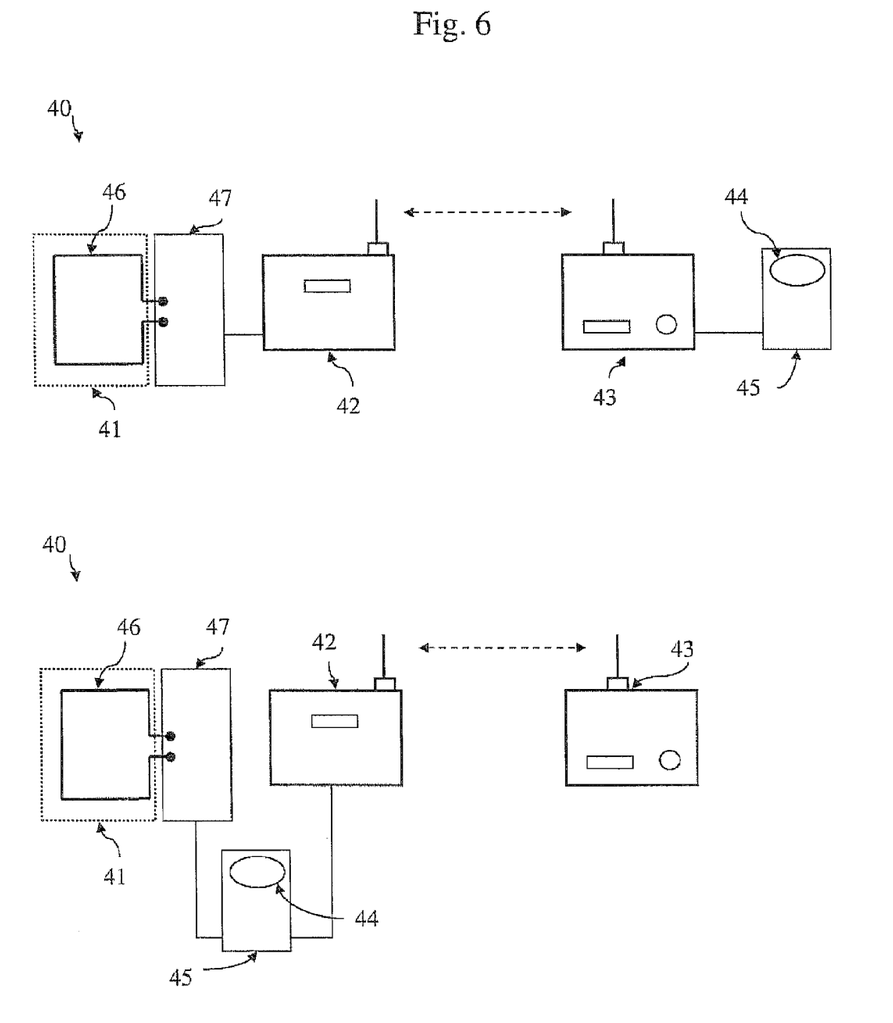
FIG. 6 shows two embodiments of the system.

The system comprises a transmitter (42) for sending an output signal of the sensor (41) to a receiver (43) as is shown for two embodiments in FIG. 6. Although the sending may be performed along an electrically conductive wire or along an optical fiber connecting the transmitter and the receiver, it is preferred that the transmission of the signal between transmitter and receiver is wireless. The system comprises an output unit (47) for providing an output signal of the sensor that is representative of the inductance of the conductive loop (46). This output signal may be the measured inductance, but it may be also a signal that is corrected by the calibration data. The system further comprise a memory (44) for storing data. Such a memory may be directly connected with the sensor as shown in the lower drawing or it may be directly connected to the receiver as shown in the upper drawing. In addition to the memory, the system comprise a processor (45) for calculating the degree of torsion or bending.

The wireless transmission of the data has the advantage that the animal or human is not hindered by wires during the measurement. This is in particular importance when the torsion or bending is measured during walking or even running. Any type of wireless transmitter can be used, including infrared, but a radio transmitter may be preferred because of its range and because the reception of the signal is hardly hindered by possible objects situated between the transmitter and the receiver.

The system may comprise one or more additional sensors for measuring the torsion or bending in a static situation, viz. when the animal or human is at rest. Such sensors may be accelerometers, resistive bending sensors or optical sensors. The sensor may be placed at a position where the mechanical load or the deformation forces during motion are relatively small. Examples of such positions are the upper and lower leg when bending of a knee is measured, or the upper and lower arm when bending of an elbow is measured.

An additional sensor is in particular suited in an embodiment of the system in which the calibration of the loop is performed semi-permanently, viz. at intermediate time intervals when the part of the body is at rest.

EXAMPLE

In an embodiment of the method shown in FIG. 3, the conductive loop is a 30 centimeter by 10 centimeter rectangular coil with a single winding made out of a metallic wire, with an open end for two contacts for measuring the inductance. The inductance of this loop is measured using a 2.5 MHz oscillator. The oscillator gives a train of pulses representing the frequency which depends on the inductance sensor. The inductance sensor is connected in series with a second coil of Ls=470 nH and a capacitance of C=5.7 nF. A counter is used to count the pulses from the oscillator in 10 ms. Suppose a measurement of N counts in 10 ms. The frequency measurement is then $$fm = N*100 \text{ in Hz}$$

the inductance is then calculated using $$2*pi*fm = 1/\text{sqrt}(L*C)$$

Or $$Lm = 1/(C*(2*i*fm)^2)$$

Hence the real bending sensor inductance is $$L = Lm - Ls$$

Figure 7:
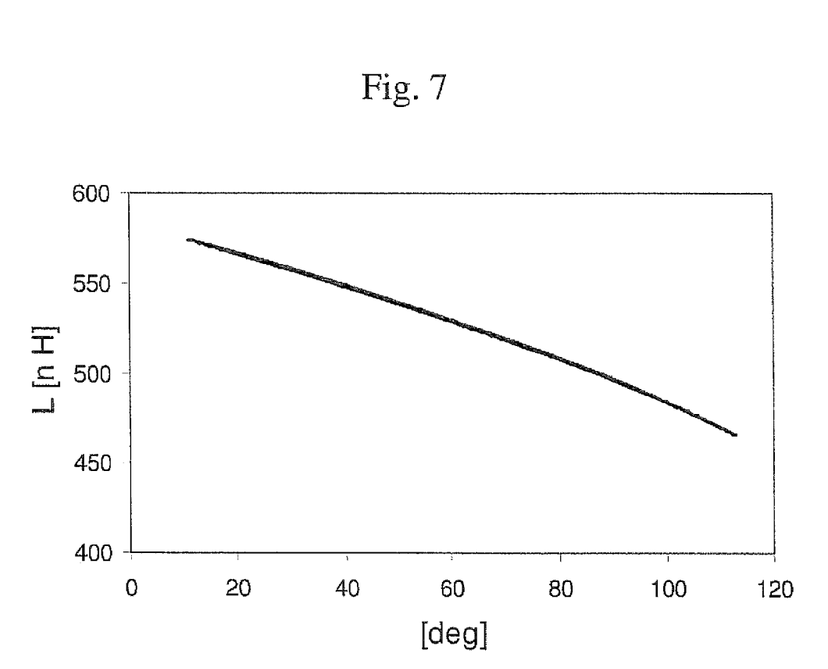
FIG. 7 shows calibration data for bending of a loop.

Typical values for the inductance L for this loop are between 400 and 600 nH. FIG. 7 shows the relation between the bending angle and the measured inductance for this embodiment. This graph is an example of calibration data that are used to calibrate the sensor for measurements under dynamic conditions, in particular for bending. In a similar way calibration data can be obtained for torsion and more complex deformations, viz. deformations with more than one degree of freedom.

Figure 8:
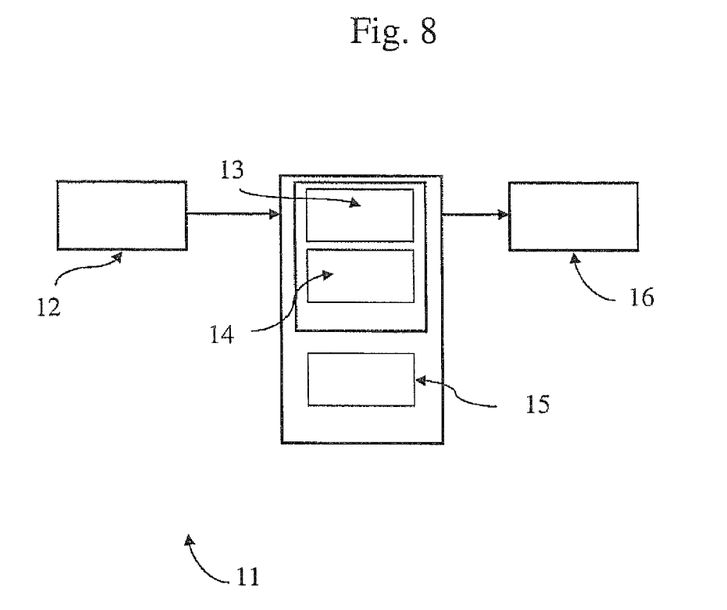
FIG. 8 illustrates a method.

FIG. 8 shows a method (11) for measuring a degree of torsion or bending of a part of a human or animal body. The method comprise a first step (12) of attaching a sensor for measuring the degree of torsion or bending to said part of the human or animal body. This is followed by a set of subsequent steps, including obtaining (13) calibration data of the sensor by detecting the output signal of the sensor for a well defined degree of torsion or bending of said part of the human or animal body, storing (14) the calibration data, measuring (15) an output signal of the sensor during torsion or bending of said part of the human or animal body, and a final step (16) of relating said output signal of the sensor to a degree of torsion or bending by using the calibration data. herein the sensor (41, 56) comprises an electrically conductive loop (46, 51), the area of said loop at least partially covering said part of the human or animal body, and an output unit (47, 58) for providing an output signal that is a measure for the inductance of the loop.

According to one aspect a method (11) for measuring a degree of torsion or bending of a part of a human or animal body is provided, the method comprising a first step (12) of attaching a sensor for measuring the degree of torsion or bending to said part of the human or animal body, subsequent steps, comprising obtaining (13) calibration data of the sensor by detecting the output signal of the sensor for a well defined degree of torsion or bending of said part of the human or animal body, storing (14) the calibration data, measuring (15) an output signal of the sensor during torsion or bending of said part of the human or animal body, a final step (16) of relating said output signal of the sensor to a degree of torsion or bending by using the calibration data, characterised in that the sensor (41, 56) comprises an electrically conductive loop (46, 51), the area of said loop at least partially covering said part of the human or animal body, and an output unit (47, 58) for providing an output signal that is a measure for the inductance of the loop.

In an embodiment the well defined degree of torsion or bending is measured by using an accelerometer when the part of the human or animal body is preferably substantially at rest.

According to another aspect a system (40) for measuring a degree of torsion or bending of a part of a human or animal body is provided, the system comprising a sensor (41) for measuring the degree of torsion or bending under dynamic and static conditions, a transmitter (42) for sending an output signal of the sensor that is representative for the measured degree of torsion or bending to a receiver, a receiver (43) for receiving the sent output signal, a memory (44) for storing data, a processor (45) for calculating the degree of torsion or bending of said part of the human or animal body, characterised in that the sensor comprises an electrically conductive loop (46) with an area for covering at least partially said part of the human or animal body, and an output unit (47) for providing an output signal that is a measure for the inductance of the loop. In an embodiment the transmitter is a wireless transmitter. In an alternative or further embodiment the system comprises a second sensor for measuring the degree of torsion or bending under static conditions.

According to another aspect a brace for measuring a degree of torsion or bending of a part of a human or animal body is provided, the brace comprising a sensor (56) for measuring the degree of torsion or bending under dynamic and static conditions, a transmitter (57) for sending an output signal of the sensor that is representative for the measured degree of torsion or bending to a receiver, characterised in that the sensor comprises an electrically conductive loop (51) with an area for covering at least partially said part of the human or animal body, and an output unit (58) for providing an output signal that is a measure for the inductance of the loop. In an embodiment the brace comprises a second sensor for measuring a degree of torsion or bending under static conditions.

A desirable objective is to provide a method for measuring a degree of torsion or bending of a part of a human or animal body that allows accurate measuring of the torsion or bending in dynamic situations, viz. while the human or animal is moving. More in particular it is a desirable objective to provide a method that allows the detection of a large angle torsion or bending.

This objective is obtained by the method according to the preamble which is characterised in that the sensor comprises an electrically conductive loop, the area of said loop at least partially covering said part of the human or animal body, and an output unit for providing an output signal that is a indicative of the inductance of the loop.

An advantage of an electrically conductive loop is that such a loop can be made mechanically very flexible and that bending with large angles is possible without damaging the loop. An effect of using a flexible loop is that the sensor can be deformed to a large extent without being damaged.

The above mentioned objective is obtained with this effect because the large deformation of the sensor allows measuring a large bending of a knee, an elbow or other parts of the human or animal body or measuring large torsion angles of for example the torso or neck.

Another desirable objective is providing a system for accurate measuring of a degree of torsion or bending of a part of a human or animal body in a dynamic situation, viz. while the human or animal is moving. More in particular it is a desirable objective to provide a system that allows the detection of a large angle torsion or bending in such a dynamic situation.

This objective is obtained with the system according to the preamble which is characterised in that the sensor comprises an electrically conductive loop with an area for covering at least partially said part of the human or animal body, and an output unit for providing an output signal that is a measure for the inductance of the loop.

An advantage of an electrically conductive loop for sensing the torsion or bending is that such a loop can be made mechanically very flexible. An effect of using a flexible loop with an area for covering at least partially the relevant body part, is that the sensor can be deformed to a large extent without being damaged. The flexibility also results in a high sensitivity for any kind of deformation, in particular for torsion and bending.

The above mentioned objective is obtained with this effect because the large deformation of the sensor allows measuring a large bending of a knee, an elbow or other parts of the human or animal body or measuring large torsion angles of for example the torso or neck. The high sensitivity also attributes to an accurate determination of the torsion or bending.

A third desirable objective is providing a brace for accurate measuring of a degree of torsion or bending of a part of a human or animal body in a dynamic situation, viz. while the human or animal is moving. More in particular it is a desirable objective to provide a brace that allows the detection of a large angle torsion or bending in such a dynamic situation.

This third objective is obtained with the brace mentioned above characterised in that the sensor comprises an electrically conductive loop with an area for covering at least partially said part of the human or animal body, and output unit for providing an output signal that is a measure for the inductance of the loop.

An advantage of an electrically conductive loop for sensing the torsion or bending is that such a loop can be made mechanically very flexible and thus very well suited for use in a flexible brace, in particular in a brace made out of a fabric. The flexible loop will hardly influence the mechanical properties of the brace. An effect of using a flexible loop with an area for at least partially covering the relevant body part is that the sensor can be deformed to a large extent without being damaged or without influencing the torsion or bending. The flexibility also results in a high sensitivity for any kind of deformation, in particular for torsion and bending.

The above mentioned objective is obtained with this effect because the large deformation of the sensor allows measuring a large bending of a knee, an elbow or other parts of the human or animal body or measuring large torsion angles of for example the torsos or neck. The high sensitivity also attributes to an accurate determination of the torsion or bending, which torsion or bending will hardly be influenced by the loop.

FIGS. 9A-C and 10A-C show different embodiments of the sensing loop. A first and second limbs 90, 92 joined by a joint are shown. For example, limbs 90, 92 may be a human thigh and shin respectively. A virtual common axial line of limbs 90, 92 can be distinguished within the limbs 90, 92 (indicated by a dashed line 99), the common axial line running along the axis of first limb 90 to the axis of second limb 92 through the joint, so that the joint affects the angle between the axes in the common axial line. A brace 94 is provided. For the sake of illustration brace 94 is shown only in FIGS. 9A, 10A. It should be understood could also have been shown in the other FIGS. 9B,C 10B,C but has been omitted from these drawings. As used herein, a brace is a structure that is attached to the limbs 90, 92 on both sides of a joint, for example by means of bands around the limbs 90, 92, and extends from one limb to the other at least partly in contact with the surface of the limb.

Figure 9:
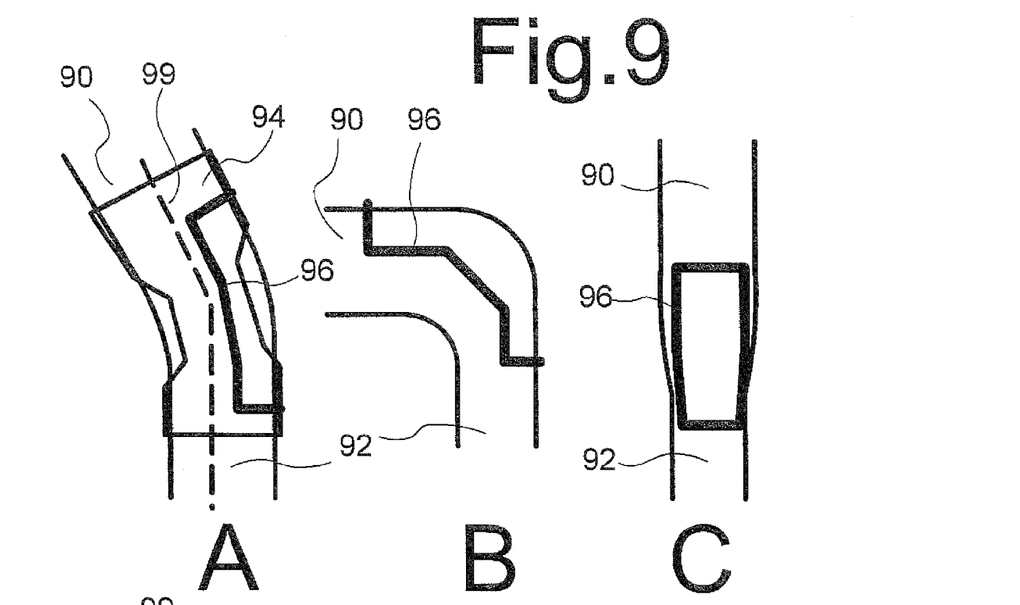
FIG. 9 shows an embodiment of a sensing loop
Figure 10:
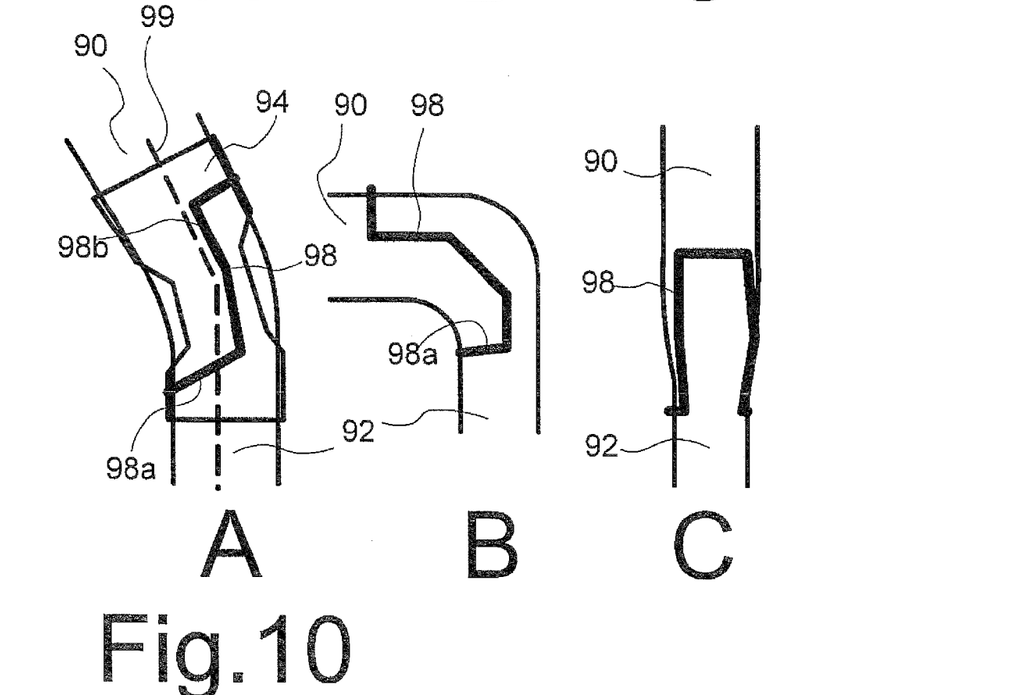
FIG. 10 shows a further embodiment of a sensing loop

FIGS. 9A-C show the sensing loop described in the preceding as loop 96. FIGS. 10A-C show and alternative sensing loop 98. The sensing loops 96, 98 lie in brace 94, possibly on its surface. As used herein "lying in" brace 94 covers lying on the surface of brace 94. The sensing loops 96, 98 run substantially in parallel to the surface of first and second limbs 90, 92 and their joint. The sensing loops 96, 98 each have a first and second part that run at mutually different positions from first limb 90 to second limb 92 over the joint. Furthermore, sensing loops 96, 98 have third and fourth parts that run between the first and second parts, on the first and second limbs respectively.

In the embodiment of FIGS. 9A-C the third and fourth part run on the same side of limbs 90, 92, so that the sensor loop does not encircle the common axial line of the limbs 90, 92. In the embodiment of FIGS. 10A-C the third part 98a of the sensor loop 98 and the fourth part 98b of the sensor loop 98 run on mutually opposite sides of the limbs 90, 92. A loop area can be defined which is a two dimensional area (which may be curved in three dimensions) whose edge is formed by the sensor loop 96, 98. A surface part of the loop area can be defined that is a collection of the points on lines in a loop area between pairs of points along the loop, where the lines run along the surface of the limbs 90, 92 and the joint, and where the lines are the shortest such lines within the loop area that do not intersect the loop between the pairs of points.

In the embodiment of FIGS. 9A-C the surface part of the loop area is a complete loop area of the sensor loop 96, which lies entirely on the surface of the limbs 90, 98 and joint, covering a part of the surface of first limb 90, a part of the surface of second limb 92 and extending between these parts of the surfaces between the limbs 90, 92. In the embodiment of FIGS. 10A-C the surface part of the loop area similarly has parts covering a part of the surface of first limb 90, a part of the surface of second limb 92 and extending between these parts of the surfaces between the limbs 90, 92. However, the surface part of the loop area of the sensor loop 98 of the embodiment of FIGS. 10A-C is not a complete loop area, as part of the loop area intersects the axis of second limb 92.

Compared to sensor loops (not shown) that only encircle the common axial line 99 of the limbs 90, 92, i.e. sensor loops that do not have surface part of the loop area that covers part of the surface of both limbs, a sensor loop 96, 98 that has surface part of the loop area that does extend to both limbs has the advantage that it is sensitive to more limb movements. Basically, loops that only encircle the common axial line 99 are only sensitive to bending (changes of the angle between the axes of the respective limbs 90, 92 along the common axial line 99), but not, or at most weakly, sensitive to torsion, which corresponds to rotation of limbs 90, 92 relative to each other around these axes.

The sensor loops of the embodiments of FIGS. 9A-C, 10A-C are sensitive to both bending and torsion. It has been found that the use of parts 98a,b in the sensor loop that cross to mutually opposite sides on the respective limbs, as in the embodiment of FIGS. 10A-C, has the advantage has the additional advantage that the sensitivity of the sensor loop to joint movement is significantly increased.

Each sensor loop 96, 98 may be made up of a single winding of a conductor line only, or of a plurality of windings of a conductor line or a plurality of conductor lines. The sensor loops may be complete loops, but the term "loop" as used herein also covers windings that are nearly complete, excepting for example an opening for connection to the loop, as long as the loop has parts that run on both limbs and between the limbs. Although FIGS. 9A-C and 10A-C show nearly rectangular loops with a largely convex shape, it should be understood that other patterns, including patterns with concave parts, or with zig-zagging conductors may be used. Although examples have been given in terms of application to human body joints, it will be understood that the system, method and sensor can also be applied to sensing of motion of an animal joint, or indeed of any mechanical joint of electrically isolating or resistive material.

The invention claimed is:

1. A joint motion sensing device, for use on a joint connecting a first body part of a body and a second body part of the body to detect torsion or bending of the first and second body parts relative to each other at the joint, the device comprising
   an electrically conductive loop having a first, second and third loop part, the first loop part configured to run from the first body part to the second body part along a surface of the body at a first side of the joint, the second loop part configured to run over the second body part and the third loop part configured to run from the second body part back to the first body part along the surface of the body at a second side of the joint opposite the first side, the electrically conductive loop continuing from the first loop part into the second loop part and from there into the third loop part, forming at least a part of a loop area with the first, second and third loop part at a boundary of the loop area;
   an output unit coupled to the electrically conductive loop, for providing an output signal based on inductance of the electrically conductive loop;
   a transmitter coupled to the output unit, for sending an output signal that is representative for an output of the output unit to a receiver.

2. A device according to claim 1, wherein the electrically conductive loop has a fourth loop part, configured to run over the first body part between the first and third loop part and from the first side of the joint to the second side of the joint, the electrically conductive loop continuing from the first and third loop part into the fourth loop part, the second and fourth loop parts configured to run over surface parts of the first and second body parts that face a same direction, so that the electrically conductive loop is configured to cover the surface of the body at the joint from the first side of the joint to the second side of the joint.

3. A device according to claim 2, wherein the output unit is coupled to the electrically conductive loop, the output signal being a measure of a self inductance of the electrically conductive loop formed by the first, second, third and fourth loop parts, or of a plurality of serially connected electrically conductive loops with loop parts that run in parallel with the first, second, third and fourth loop parts.

4. A device according to claim 1, wherein the electrically conductive loop has a fourth loop part, configured to run over the first body part between the first and third loop part, the electrically conductive loop continuing from the first and third loop part into the fourth loop part, the second and fourth loop parts configured to run over surface parts of the first and second body parts that face in mutually opposite directions, so that the electrically conductive loop is configured to have a combination of the body parts intersect the loop area once without returning through the loop area, whereby the combination of the body parts runs through the loop area, regardless of a degree of torsion or bending of the first and second body parts relative to each other at the joint.

5. A device of claim 4, comprising a brace mountable over the joint, encircling both the first and second body parts, wherein the electrically conductive loop lies on a surface of said brace or within said surface, encircling an inner space defined by the brace for receiving the combination of the first and second body part.

6. A device of claim 4, comprising a substrate that is configured to allow attachment to the first and second body parts, encircling both the first and second body parts, wherein the electrically conductive loop lies on a surface of said substrate or within said surface, encircling an inner space defined by the substrate for receiving the combination of the first and second body part.

7. A device according to claim 1, comprising two accelerometers, configured for positioning on the first body part and on the second body part, respectively.

8. A device according to claim 1, comprising a brace mountable over the joint attached to the first and second body parts, wherein the loop area lies on a surface of said brace or within said surface.

9. A system for detecting torsion or bending of a first body part and a second body part relative to each other, the system comprising the device of claim 1 and further comprising,
a receiver for receiving the sent output signal,
a memory for storing data,
a processor for calculating the degree of torsion or bending of said body parts relative to each other.

10. A device according to claim 1, comprising a substrate that is configured to allow attachment to the first and second body parts, wherein the loop area of the conductive loop lies on a surface of said substrate or within said surface.

11. A device according to claim 10, wherein the substrate comprises a fabric, wherein the conductive loop is attached to or integrated in the fabric.

12. A method of measuring a degree of torsion or bending of a first body part and a second body part of a body relative to each other at a joint between the body parts, the method comprising
attaching an electrically conductive loop to the body parts, the electrically conductive loop having a first, second and third loop part, the first loop part running from the first body part to the second body part along a surface of the body at a first side of the joint, the second loop part running over the second body part and the third loop part running from the second body part back to the first body part along the surface of the body at a second side of the joint opposite the first side, the electrically conductive loop continuing from the first loop part into the second loop part and from there into the third loop part, forming at least a part of a loop area with the first, second and third loop part at a boundary of the loop area;
measuring an output signal that is a measure for an inductance of the electrically conductive loop during torsion or bending,
relating said output signal of the sensor to a degree of torsion or bending by using calibration data.

13. A method according to claim 12, wherein the electrically conductive loop has a fourth loop part, running over the first body part between the first and third loop part from a first side of the joint to a second side of the joint opposite the first side, the electrically conductive loop continuing from the first and third loop part into the fourth loop part, the second and fourth loop parts running over surface parts of the first and second body parts that face a same direction, so that the loop area covers the surface of the body at the joint from the first side of the joint to the second side of the joint.

14. A method according to claim 13, wherein said measuring comprises generating an output signal that is a measure for a self inductance of the electrically conductive loop formed by the first, second, third and fourth loop parts.

15. A method according to claim 12, wherein the electrically conductive loop has a fourth loop part, running over the first body part between the first and third loop part, the electrically conductive loop continuing from the first and third loop part into the fourth loop part, the second and fourth loop parts running over surface parts of the first and second body parts that face in mutually opposite directions, so that a combination of the body parts intersects the loop area once without returning through the loop area, whereby the combination of the body parts runs through the loop area, regardless of the degree of torsion or bending of the first and second body parts relative to each other at the joint.

16. A method according to claim 12, comprising providing a first and a second accelerometer positioned on the first body part and on the second body part, respectively for measuring an angle between the first and second body parts indirectly by determining directions of gravitational force relative to the first and the second body part under static conditions, and determining the calibration data using said direction.

17. A method according to claim 12, wherein the first and second body parts and their joint are a part of a human or animal body.

18. A method according to claim 17, wherein the joint is a knee joint of the human or animal body.

* * * * *